US010242467B2

United States Patent
Nishiyama et al.

(10) Patent No.: US 10,242,467 B2
(45) Date of Patent: Mar. 26, 2019

(54) OPTICAL TOMOGRAPHY APPARATUS

(71) Applicant: NIDEK CO., LTD., Gamagori, Aichi (JP)

(72) Inventors: Junpei Nishiyama, Gamagori (JP); Seigo Ueda, Gamagori (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 38 days.

(21) Appl. No.: 15/446,147

(22) Filed: Mar. 1, 2017

(65) Prior Publication Data

US 2017/0256078 A1 Sep. 7, 2017

(30) Foreign Application Priority Data

Mar. 2, 2016 (JP) .................. 2016-040516

(51) Int. Cl.
*G06K 9/00* (2006.01)
*A61B 3/14* (2006.01)
(Continued)

(52) U.S. Cl.
CPC ............ *G06T 11/008* (2013.01); *A61B 3/102* (2013.01); *A61B 5/0066* (2013.01); *G06T 3/0006* (2013.01); *G06T 5/003* (2013.01); *G06T 5/006* (2013.01); *G06T 5/50* (2013.01); *G06T 7/30* (2017.01); *G06T 2207/10016* (2013.01); *G06T 2207/10101* (2013.01); *G06T 2207/20182* (2013.01); *G06T 2207/20201* (2013.01);
(Continued)

(58) Field of Classification Search
USPC ........ 382/100, 103, 106–107, 128–134, 154, 382/155, 162, 168, 173, 181, 189, 382/219–220, 232, 254, 274, 276, 382/286–291, 305, 321; 378/4, 21; 351/206, 240; 348/78; 356/479
See application file for complete search history.

(56) References Cited

U.S. PATENT DOCUMENTS

2009/0185191 A1* 7/2009 Boppart ............... A61B 5/0066
356/479
2010/0110171 A1* 5/2010 Satake .................. A61B 3/102
348/78
(Continued)

FOREIGN PATENT DOCUMENTS

JP 2010110392 A 5/2010
JP 2014188276 A 10/2014

*Primary Examiner* — Seyed H Azarian
(74) *Attorney, Agent, or Firm* — Sughrue Mion, PLLC

(57) ABSTRACT

An optical tomography apparatus has a measurement unit that divides light output from a light source into measurement light and reference light, that repeatedly scans a subject with the measurement light, and that causes a detector to detect interference between reflected light of the measurement light and the reference light, and a processor. The processor performs an acquisition process of are temporally sequentially acquiring tomographic images at the same transverse position in the subject based on a signal output from the detector. The processor performs a video image generation process of generating a synthetic image on a real time basis by synthesizing a new tomographic image frequently and one or more past images, and causing a monitor to display a real time video image formed from the synthetic image.

14 Claims, 7 Drawing Sheets

(51) Int. Cl.
*G06T 11/00* (2006.01)
*G06T 7/30* (2017.01)
*A61B 5/00* (2006.01)
*G06T 3/00* (2006.01)
*G06T 5/00* (2006.01)
*A61B 3/10* (2006.01)
*G06T 5/50* (2006.01)

(52) U.S. Cl.
CPC ............... *G06T 2207/20216* (2013.01); *G06T 2207/20221* (2013.01); *G06T 2207/30041* (2013.01); *G06T 2210/41* (2013.01)

(56) References Cited

U.S. PATENT DOCUMENTS

| | | | |
|---|---|---|---|
| 2014/0300864 A1* | 10/2014 | Fukuma | A61B 3/102 351/206 |
| 2014/0320810 A1* | 10/2014 | Fukuma | A61B 3/0008 351/206 |
| 2015/0182111 A1* | 7/2015 | Namiki | A61B 3/102 351/206 |
| 2018/0300864 A1* | 10/2018 | Baba | G06T 7/001 |

\* cited by examiner

OPTICAL TOMOGRAPHY APPARATUS

CROSS REFERENCE TO RELATED APPLICATION

This application is based upon and claims the benefit of priority of Japanese Patent Application No. 2016-040516 filed on Mar. 2, 2016, the contents of which are incorporated herein by reference in its entirety.

BACKGROUND ART

This disclosure relates to an optical tomography apparatus which captures a tomographic image of a tissue of a subject.

In the related art, as an apparatus which can capture a tomographic image in a predetermined site of a subject, an apparatus using optical coherence tomography (OCT) is known. An optical tomography apparatus using OCT divides light emitted from a light source into measurement light and reference light, and performs irradiation while scanning the tissue of the subject with the divided measurement light. The measurement light reflected from the tissue is synthesized with the reference light so as to acquire information in a depth direction of the tissue from an interference signal of the synthesized light. The optical tomography apparatus can generate the tomographic image by using the acquired information in the depth direction.

For example, JP-A-2010-110392 discloses a method of generating a still image having reduced noise by adding and averaging a plurality of tomographic images relating to a predetermined cut section.

As one type of the optical tomography apparatus, a probe-type apparatus is known which captures the tomographic image of the tissue from the inside of the subject by irradiating the tissue with the measurement light emitted from a distal end of a probe capable of being inserted into the subject (refer to JP-A-2014-188276).

[Patent Document 1] JP-A-2010-110392
[Patent Document 2] JP-A-2014-188276

The apparatus disclosed in JP-A-2010-110392 mainly obtains the still image as a result of an averaging process.

On the other hand, as one of various purposes, it is expected that the probe-type apparatus (for example, refer to JP-A-2014-188276) is used in order to observe an internal structure of the tissue which is less likely to be observed by a surgical microscope and an endoscope during surgery, for example. That is, as the purpose, it is assumed that the tomographic images of the tissue which are sequentially captured via the probe inserted into the subject are displayed as a video image (also referred to as an observation image) on a real time basis. However, the video image obtained by the probe-type apparatus has some factors, for example, such as noise, uneven scanning caused by a measurement light scanner, and relative displacement between the subject and the probe while the video image is captured. It is conceivable that any one of these factors affects visibility of the video image.

SUMMARY

This disclosure is made in view of at least one of the problems in the related art. A technical object is to provide a probe-type optical tomography apparatus which outputs a satisfactory observation image.

An optical tomography apparatus according to this disclosure includes a measurement unit that divides light output from a light source into measurement light and reference light, repeatedly scans a subject with the measurement light, and causes a detector to detect interference between reflected light of the measurement light and the reference light; and a processor, wherein the processor performs an acquisition process of temporally sequentially acquiring a plurality of tomographic images at the same transverse position in the subject are based on a signal output from the detector, and wherein the processor performs a video image generation process of generating a synthetic image on a real time basis by synthesizing a new tomographic image frequently obtained by the acquisition process and one or more past images which are the tomographic images acquired in the past prior to the new tomographic image and which are included in a range of a predetermined number of sheets whose acquisition timing is sequential to acquisition timing of the new tomographic image, and causing a monitor to display a real time video image formed from the synthetic image.

DESCRIPTION OF ILLUSTRATIVE EMBODIMENTS

Hereinafter, an embodiment according to this disclosure will be described with reference to the drawings.

Figure 1:
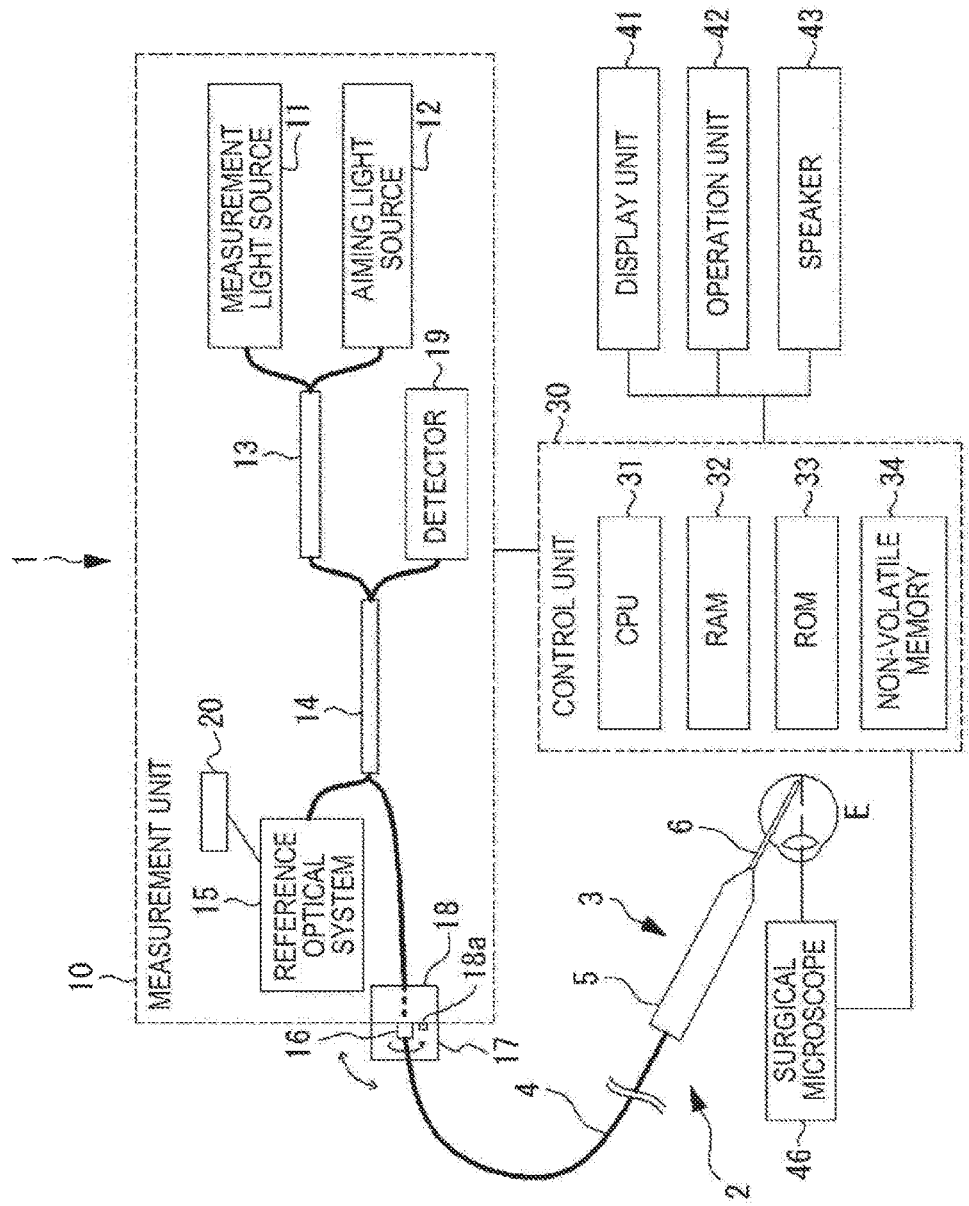
FIG. 1 is a view illustrating a schematic configuration of an optical tomography apparatus and peripheral equipment.

First, referring to FIG. 1, a schematic configuration of an optical tomography apparatus (hereinafter, abbreviated as an "imaging apparatus") 1 according to the present embodiment will be described. The imaging apparatus 1 captures a tomographic image (B-scan image) of a tissue inside a subject by using a probe 2 inserted into the subject.

Hereinafter, as a specific example, it is assumed that the imaging apparatus 1 is an ophthalmic imaging apparatus. That is, a tomographic image of an internal tissue (for example, a retina) of a subject's eye E is captured by the imaging apparatus 1. However, this disclosure is also applicable to an apparatus for capturing the tomographic image of a subject other than the eye (for example, internal organs and ears). The imaging apparatus 1 includes a measurement unit 10 and a control unit 30.

The measurement unit 10 includes a configuration (for example, an interference optical system) of optical coherence tomography (OCT). The measurement unit 10 according to the present embodiment includes a measurement light source 11, an aiming light source 12, a coupler 13, a coupler 14, a reference optical system 15, a mounting unit 16, a fiber rotating motor 18, a detector (light receiving element) 19, and an optical path length changing unit 20.

The measurement light source 11 emits light for acquiring the tomographic image. As an example, the imaging apparatus 1 according to the present embodiment includes the measurement light source 11 which can rapidly change a wavelength of laser light to be emitted, thereby acquiring the tomographic image by means of swept-source OCT (SS-OCT) measurement. The measurement light source 11 according to the present embodiment is configured to include a laser medium, a resonator, and a wavelength selection fiber. For example, as the wavelength selection fiber, it is possible to employ a combination of a diffraction grating and a polygon mirror or a filter using a Fabry-Perot etalon.

The aiming light source 12 emits aiming light serving as visible light for indicating an irradiation position of measurement light (that is, a capturing position of the tomographic image).

The coupler 13 matches optical axes of two light of the light emitted from the measurement light source 11 and the aiming light emitted from the aiming light source 12. The coupler 14 divides the light incident from the coupler 13 into the measurement light (sample light) and reference light. The measurement light is guided to the probe 2 mounted on the mounting unit 16. The reference light is guided to the reference optical system 15. The coupler 14 synthesizes the measurement light (reflected measurement light) reflected from the subject's eye E and the reference light generated by the reference optical system 15, thereby generating interference light. The coupler 14 causes the detector 19 to receive the generated interference light.

The reference optical system 15 causes the reference light guided from the coupler 14 to return to the coupler 14 again. The reference optical system 15 may be a reflection optical system (refer to JP-A-2014-188276) or a transmission optical system (refer to JP-A-2010-220774).

The measurement unit 10 has an optical path length changing unit 20 which changes an optical path length difference between the measurement light and the reference light.

The detector 19 detects an interference state between the reflected measurement light and the reference light. In other words, the detector 19 detects an interference signal of the interference light generated by the coupler 14. More specifically, in a case of Fourier domain OCT, spectral intensity of the interference light is detected by the detector 19, and Fourier transform is performed on spectral intensity data, thereby acquiring a depth profile (A-scan signal) in a predetermined range. The depth profile is collected at each scanning position, and the depth profiles are arrayed, thereby forming the tomographic image (B-scan image, refer to FIG. 3).

As described above, the imaging apparatus 1 according to the present embodiment employs SS-OCT. However, the imaging apparatus 1 can employ various types of OCT. For example, the imaging apparatus 1 may employ either spectral-domain OCT (SD-OCT) or time-domain OCT (TD-OCT). In a case of employing SS-OCT, it is desirable to employ an equilibrium detector having a plurality of light receiving elements as the detector 19. In a case of using the equilibrium detector, the imaging apparatus 1 can reduce unnecessary noise included in the interference signals by obtaining a difference between the interference signals output from the plurality of light receiving elements. As a result, quality of the tomographic image is improved.

A rear end portion (proximal end portion) of a fiber 4 in the probe 2 is detachably mounted on the mounting unit (for example, a connector) 16. The probe 2 is mounted on the mounting unit 16, thereby connecting a light guide (for example, the fiber 4 inside the measurement unit 10) of the measurement light divided by the coupler 14 and the probe 2 to each other.

The fiber rotating motor (hereinafter, abbreviated as a "motor") 18 can cause the mounting unit 16 having the fiber 4 mounted thereon to rotate about an axis of the fiber 4. That is, the motor 18 rotates the mounting unit 16, thereby rotating the fiber 4. As a result, according to the present embodiment, the measurement light and the aiming light are used in scanning (details to be described later). A rotation detection sensor 18a is disposed in the motor 18. The rotation detection sensor 18a detects the rotation of the fiber 4 in the rear end portion whenever the fiber 4 rotates once, and outputs a signal to the control unit 30 whenever the rotation is detected (that is, every one rotation). The signal output from the rotation detection sensor 18a is used in order to determine timing for starting to generate the respective tomographic images (B-scan images).

Figure 2:
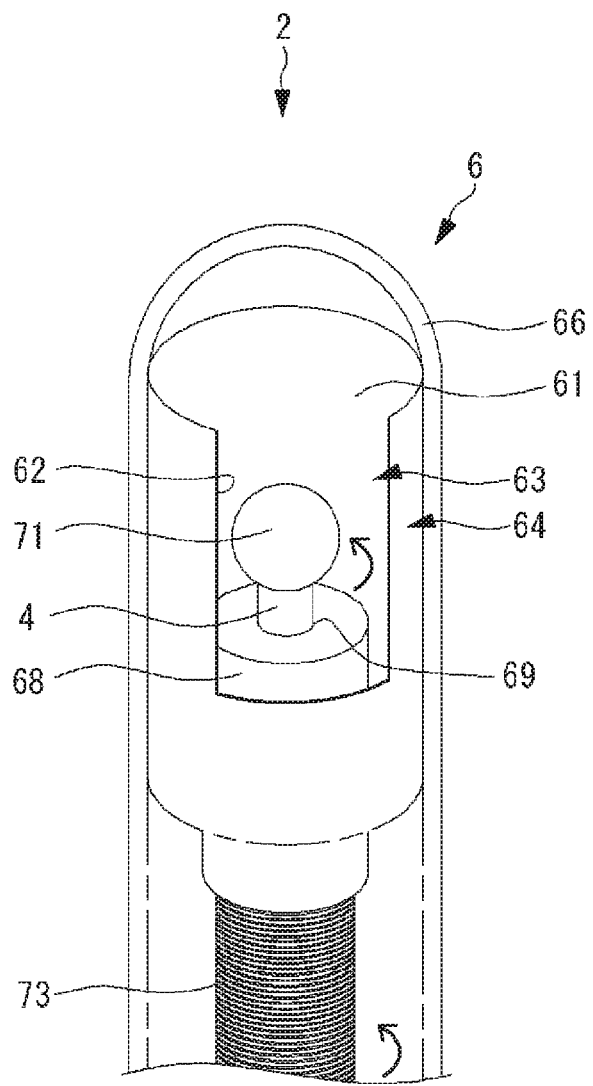
FIG. 2 is an enlarged view in the vicinity of a distal end portion of a probe.

Here, referring to FIGS. 1 and 2, the probe 2 mounted on the mounting unit 16 will be described. The probe 2 according to the present embodiment includes a probe body 3 and the fiber 4. The probe body 3 has a handpiece 5 and a needle 6.

The fiber 4 is inserted into the probe body 3, and guides the measurement light and the aiming light which are guided from the coupler 14 of the measurement unit 10 from the outside of the probe body 3 to a distal end portion of the needle 6.

The fiber 4 is coated with a torque coil (not illustrated). The torque coil is an example of a torque transmission portion, and transmits a torque output from the motor 18 to the fiber 4. In this manner, the fiber 4 rotates together with the torque coil. According to the present embodiment, the fiber 4 and the torque coil freely rotate with respect to the handpiece 5.

The handpiece 5 is a substantially cylindrical member gripped by s worker (for example, an examiner or an operator). The needle 6 is disposed in a distal end of the handpiece 5, and has an outer diameter smaller than an outer diameter of the handpiece 5. A distal end portion of the needle 6 is inserted into the subject (for example, the subject's eye E). The fiber 4 is connected to a rear end portion of the handpiece 5, and extends to the distal end portion of the needle 6. While the probe scans the subject with the measurement light and the aiming light which are guided by the fiber 4, the probe 2 can emit each light from the distal end portion.

Here, referring to FIG. 2, a structure of the distal end portion in the probe 2 will be described in more detail. The distal end portion of the needle 6 has a light blocking member 61, an outer cylinder 66, a holder 68, and a deflector 71.

The light blocking member 61 encloses the periphery (particularly, the periphery of the holder 68 and the deflector 71) on the distal end side of the fiber 4. According to the present embodiment, a shape of the light blocking member 61 is substantially cylindrical. The light blocking member 61 is formed of a material which blocks the measurement light and the aiming light. In the light blocking member 61, a notch 62 (or an opening) having a predetermined width in a scanning direction (direction around the axis) of the measurement light and the aiming light is formed in the vicinity of a portion where the deflector 71 is located in an axial direction. The light reflected from the deflector 71 is transmitted outward in a region 63 (hereinafter, referred to as a "light transmitting region 63") inside the notch 62. However, the light is blocked by the light blocking member 61 in a region 64 (hereinafter, referred to as a "light blocking region 64") where the notch 62 is not formed.

According to the present embodiment, an inner side surface of the light blocking member 61 is subjected to roughing. That is, the inner side surface of the light blocking member 61 has many minute irregularities. In this case, the light emitted to the inner side surface of the light blocking member 61 is scattered in the light blocking region 64. Therefore, compared to a case where the light is less likely to be scattered from the inner side of the light blocking member 61 (for example, a case where the inner side surface is subjected to polishing), a possibility decreases that the light reflected from the light blocking region 64 may not return to the deflector 71. That is, in the case where the inner side surface is subjected to polishing, if the light is reflected in a direction different from that of the deflector 71, the reflected light is not incident on the deflector 71. If the reflected light is scattered, the reflected light is likely to return to the deflector 71. Accordingly, in a case where the imaging apparatus 1 detects that light blocking region 64 is irradiated with the measurement light, the imaging apparatus 1 can reliably perform detection by using the light reflected from the light blocking region 64.

A shape of light transmitting region 63 according to the present embodiment is substantially rectangular. However, as a matter of course, a size, a shape, and the number of the light transmitting regions 63 can be changed. A specific method for forming the light transmitting region 63 and the light blocking region 64 can also be changed. For example, the light transmitting region 63 and the light blocking region 64 may be formed by manufacturing the light blocking member 61 in combination with a material for transmitting the measurement light and the aiming light and a material for blocking the light.

The outer cylinder 66 is formed of a material which transmits the measurement light and the aiming light, and closes the outer side of the light blocking member 61. Therefore, while preventing the tissue such as blood and a vitreous body from entering the inner side, the outer cylinder 66 allows the light to be transmitted between the inner side and the outer side of the light transmitting region 63. The outer cylinder 66 may be located inside the light blocking member 61.

The holder 68 is a member having a substantially columnar outer shape, and is fixed to the light blocking member 61. A through-hole 69 penetrating the fiber 4 in a rotatable state is formed in an axis portion of the holder 68. The holder 68 holds the fiber 4 so as to be rotatable in a state where an axial position of the fiber 4 is constantly maintained with respect to the light blocking member 61.

The deflector 71 is disposed in the distal end portion of the fiber 4. The deflector 71 deflects the light emitted from the distal end portion of the fiber 4. The light deflected by the deflector 71 is used in irradiating the tissue of the subject when passing through the light transmitting region 63. According to the present embodiment, the light deflected by the deflector 71 is collected in a predetermined distance. For example, the deflector 71 may be a ball lens or may be a prism. The deflector 71 receives the reflected measurement light reflected from the tissue, and causes the reflected measurement light to be incident on the fiber 4. The deflector 71 according to the present embodiment deflects the light at an angle of approximately 70 degrees with respect to the axial direction of the fiber 4, but the deflection angle can be appropriately changed. In the fiber 4, a torque coil 73 is disposed on the outer periphery of the portion on the rear end side from the holder 68. The torque coil 73 is used in order to transmit the rotation of the motor 18 to the fiber 4.

In the imaging apparatus 1, the measurement unit 10 or the probe 2 may include various configurations such as an optical system for adjusting a focus of the measurement light. Detailed description thereof will be omitted.

Next, referring to FIG. 1, a control system of the apparatus will be described. The control unit 30 includes a CPU (processor) 31, a RAM 32, a ROM 33, and a non-volatile memory 34. The CPU 31 controls the imaging apparatus 1 and peripheral equipment. The RAM 32 temporarily stores various pieces of information. The ROM 33 stores various programs and initial values. The non-volatile memory 34 is a non-transitory storage medium capable of storing stored content even if power supply is cut off. For example, as the non-volatile memory 34, it is possible to use a hard disk drive, a flash ROM, a USB memory mounted on the imaging apparatus 1 so as to be detachable therefrom. The non-volatile memory 34 stores an imaging control program for controlling a main process (to be described later, refer to FIG. 6). The non-volatile memory 34 stores various types of information such as the captured tomographic image.

As the control unit 30, the present embodiment employs a personal computer (hereinafter, referred to as a "PC") connected to the measurement unit 10. However, without using the PC, the measurement unit 10 and the control unit 30 may be integrated with each other as a single device. The control unit 30 may be configured to include a plurality of control units (that is, a plurality of processors). For example, the control unit 30 of the imaging apparatus 1 may be configured to include a first control unit disposed in the PC and a second control unit disposed inside the measurement unit 10. In this case, for example, the first control unit of the PC may instruct the second control unit to start and finish the imaging, based on an operation of an operation unit connected to the PC. The second control unit may control each operation of the measurement light source 11, the aiming light source 12, and the motor 18, in accordance with the instruction from the first control unit. An image generation process based on the interference signal may be performed by any one of the first control unit and the second control unit.

The peripheral equipment such as a display unit 41 (monitor), an operation unit 42, and a surgical microscope 46 is electrically connected to the control unit 30. The display unit 41 displays the tomographic image (to be described later). The display unit 41 may be a display of the PC, or may be a display dedicated to the imaging apparatus 1. The display unit 41 may be configured so that a plurality of displays are used in common. The operation unit 42 serves as a device for recognizing various operation instructions given by a worker. For example, the operation unit 42 may employ at least one of a mouse, a joystick, a keyboard, and a touch panel.

According to the present embodiment, the control unit 30 also serves as an image forming unit for forming the tomographic image, based on a signal output from the detector 19. In this case, for example, the control unit 30 performs Fourier transform on the signal output from the detector 19, thereby acquiring a depth profile (A-scan) and arraying the depth profile acquired at each scanning position. In this manner, the control unit 30 generates the tomographic image (B-scan image). According to the present embodiment, since the scanning is performed around the axis of the probe 2, each depth profile is expressed using a polar coordinate system whose origin is placed on the axis of the probe 2. The control unit 30 may acquire tomographic image data of the subject which is expressed using the polar coordinate system. More specifically, the control unit 30 may acquire the tomographic image in the polar coordinate system in which a horizontal axis of the image corresponds to an angle and a vertical axis corresponds to a depth as illustrated in FIG. 3.

Figure 4:
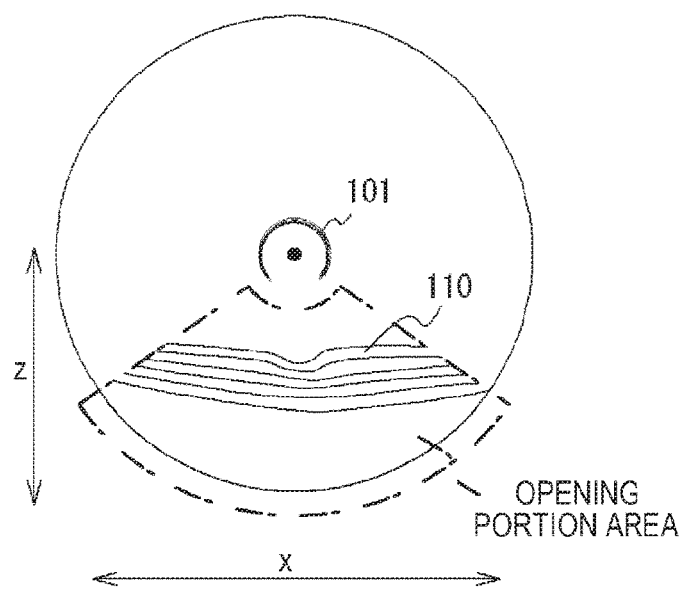
FIG. 4 is a view schematically illustrating a tomographic image expressed using a Cartesian coordinate.

Instead of the tomographic image expressed using the polar coordinate system, the control unit 30 may acquire the tomographic image expressed using a Cartesian coordinate. As illustrated in FIG. 4, the tomographic image expressed using the Cartesian coordinate described herein is expressed so that axes orthogonal to each other (for example, an X-axis (axis in a horizontal direction)) and a Z-axis (axis in a depth direction) in an actual space are also orthogonal to each other on the image. For example, the tomographic image expressed using the Cartesian coordinate in this way may be transformed from the tomographic image expressed using the polar coordinate system (for example, refer to JP-A-2015-104582 applied by the present applicant).

Here, referring to FIG. 3, an example of the tomographic image generated in the imaging apparatus 1 will be described.

Figure 3:
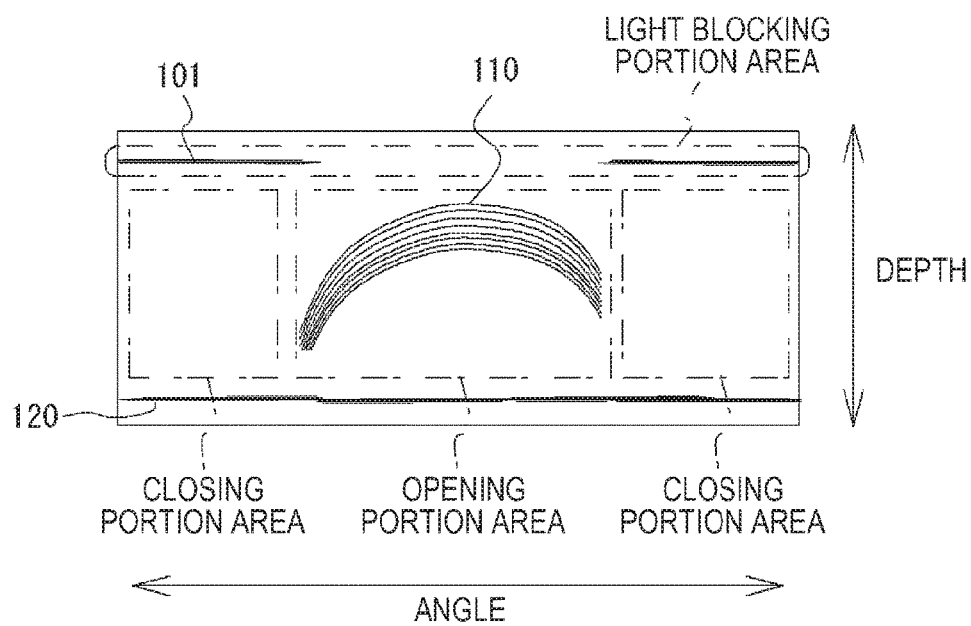
FIG. 3 is a view schematically illustrating a tomographic image expressed using a polar coordinate system.

As illustrated in FIG. 3, the tomographic image generated in the imaging apparatus 1 can be classified into some regions. An image 101 in FIG. 3 represents an internally reflected image. The internally reflected image 101 described herein is formed, based on reflection of a member inside the probe 2. According to the present embodiment, the internally reflected image 101 is formed, based on the reflection of the measurement light which is caused by the light blocking member 61 (more specifically, the light blocking region 64). For the sake of convenience in the following description, description of each region will be described with reference to the internally reflected image 101.

A closing portion area in FIG. 3 is a region which is located outside the light blocking member 61 (outside the probe 2), and at which the measurement light does not arrive due to the light blocking member 61 (light blocking region 64) (in other words, a shielded region). In the tomographic image, the closing portion area is a region whose position in a scanning direction is substantially the same as that of the internally reflected image 101, and which is located on a side separated from the probe 2 (outside the probe 2, a deeper side in the depth direction, lower side of the drawing in an example of FIG. 3) compared to the internally reflected image 101.

An opening portion area in FIG. 3 is a region which is located outside the light blocking member 61, and which is irradiated with the measurement light passing through the light blocking member 61 (more specifically, a light transmitting region (opening)). In the tomographic image, the closing portion area is a region whose position in the scanning direction is substantially the same as that of the internally reflected image 101, and which is located on the side separated from the probe 2 compared to the internally reflected image 101. An image formed in the opening portion area (image 110 of the subject) is formed by the measurement light passing through the light blocking member 61.

Incidentally, FIG. 3 illustrates an example in which a reflected image 120 (second internally reflected image) appears on the side separated from the probe 2 compared to the internally reflected image 101. For example, as a reflected portion which causes the reflected image 120 to be generated, a joint portion between the fiber 4 and a lens (not illustrated) inside the probe 2 may be considered. In this way, the reflected image 120 is generated depending on optical system design and apparatus design such as an image acquisition range in the depth direction. For example, a relative position relationship between the reflected image 120 and the internally reflected image 101 may be constant regardless of a position relationship between the probe 2 and the subject. Those skilled in the art may employ apparatus design of the optical system so that the reflected image 120 is not included in the tomographic image.

As illustrated in FIG. 3, in a case where the reflected image 120 appears in the tomographic image, at least the reflected image 120 and the vicinity region are excluded from the opening portion area and the closing portion area. For example, in the tomographic image in FIG. 3, a region existing between the internally reflected image 101 and the reflected image 120 is used as the opening portion area and the closing portion area.

The inner side area of the probe 2 illustrated in FIG. 3 represents a region where the internally reflected image 101 is disposed in the depth direction. The light blocking portion area illustrated in FIG. 3 is illustrated as a band-shaped region extending in the scanning direction at a position of the internally reflected image 101 in the depth direction, or within a range in the vicinity of the internally reflected image 101 including the internally reflected image 101. A distance between the light blocking member 61 and the distal end of the probe 2 (distal end of the needle 6, more specifically, the deflector 71) is known. Accordingly, the internally reflected image 101 and/or the light blocking portion area can be used for as a reference of the depth direction in the tomographic image in the imaging apparatus 1.

Each area in the tomographic image described above may be individually detectable (identifiable) through image processing performed by the control unit 30.

FIG. 3 illustrates an example of the tomographic image which is visualized (imaged) so that a pixel having higher signal intensity in the OCT signal has higher luminance. In the following description, unless otherwise specified, it is assumed that the tomographic image is generated so that a correspondence relationship between the signal intensity of the OCT signal and the luminance in the pixel is the same as that in FIG. 3. However, for example, as the tomographic image, an image obtained by inverting white and black colors of the image in FIG. 3 may be generated. The tomographic image obtained in this case is visualized (imaged) so that a pixel having lower signal intensity in the depth profile has higher luminance.

The surgical microscope 46 magnifies and displays the internal image of the subject (the subject's eye E in the present embodiment) during surgery, during diagnosis, or during exercises thereof. While looking into the surgical microscope 46, a worker carries out the surgery, the diagnosis, or the exercises (these are collectively referred to as "work" in the present embodiment). According to the present embodiment, the control unit 30 can acquire an image captured by the surgical microscope 46, and can display the image on the display unit 41. In this case, the worker can carry out the work while confirming the image captured by the observation optical system. This disclosure is also applicable to a case where the worker gazes at the vicinity of the distal end portion of the probe 2 with his or her naked eye.

Figure 5:
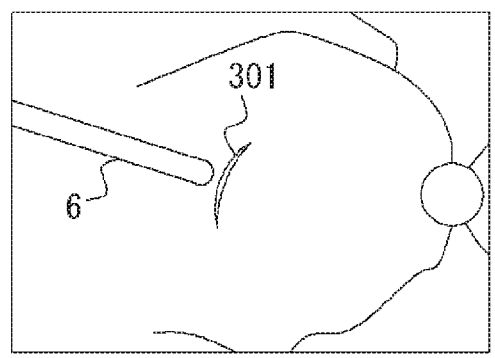
FIG. 5 is a view illustrating a fundus state confirmed by a worker when the fundus state is imaged.

According to the present embodiment, a surface of the subject is irradiated with the aiming light at a position where the tomographic image is acquired. Accordingly, a bright line 301 generated by the aiming light enables the worker to confirm an imaging position (refer to FIG. 5).

Hereinafter, referring to FIGS. 6 to 9, an operation of the imaging apparatus 1 will be described. Here, the operation will be described with reference to a flowchart in FIG. 6 which is illustrated as an example. For example, each process illustrated in FIG. 6 may be performed by the control unit 30 in accordance with a control program stored in the non-volatile memory 34, when the power of the imaging apparatus 1 is turned on.

Figure 6:
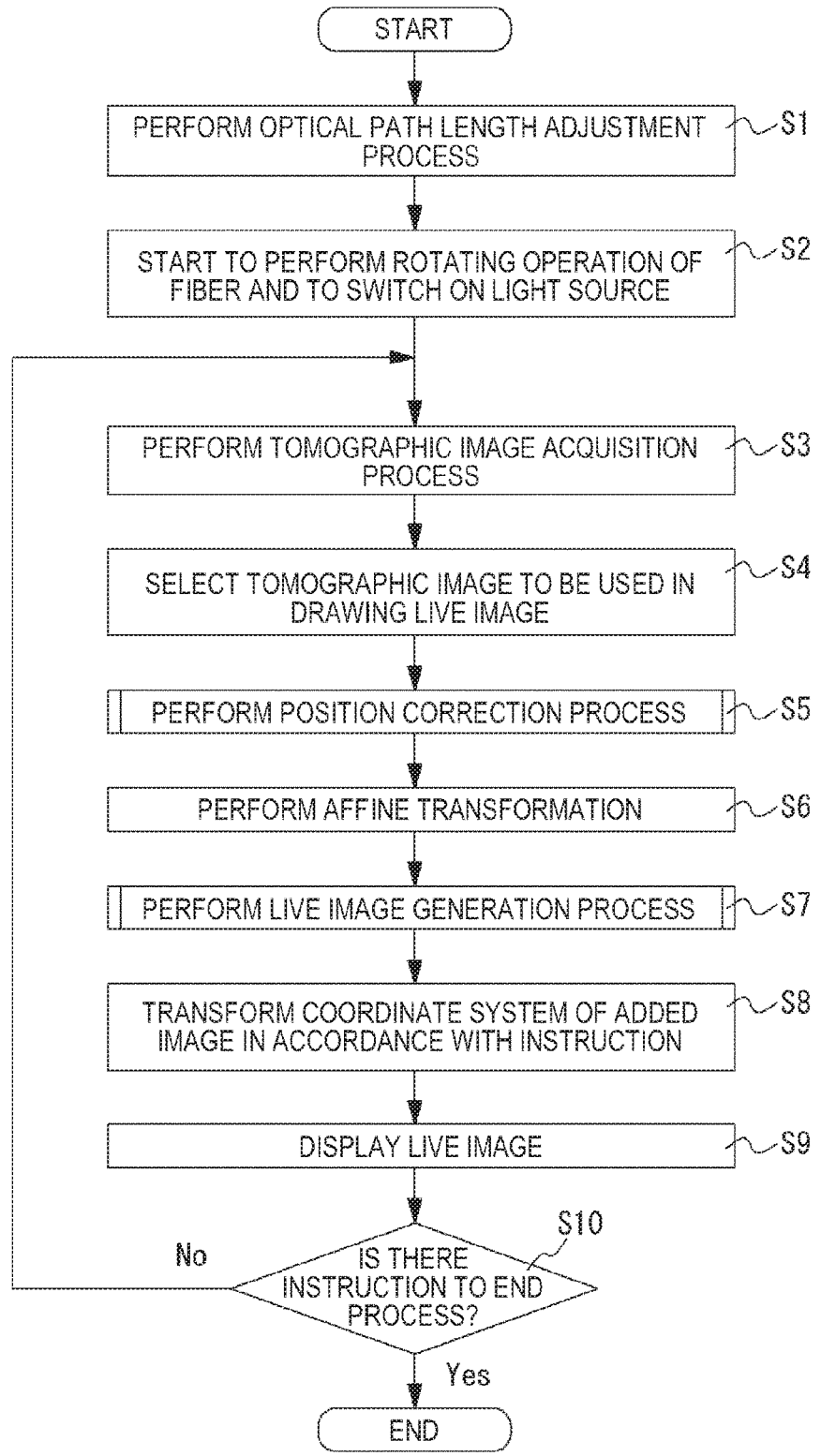
FIG. 6 is a flowchart illustrating an operation example of the optical tomography apparatus according to the present embodiment.

According to the present embodiment, the control unit 30 performs an optical path length adjustment process (S1), thereby adjusting an optical path length difference between the measurement light and the reference light. In the optical path length adjustment process (S1), the control unit 30 adjust the optical path length difference between the measurement light and the reference light by driving an optical member disposed in the optical path of the measurement light or the reference light so that an image of a predetermined reflector whose distance from the deflector 71 is known is formed in a region at a predetermined depth position in the tomographic image. For example, even in a case where the optical path length difference is changed from that of the previous image capturing due to exchange of the fiber 4 (or the probe 2 including the fiber 4), in accordance with a result of the process in S1, an image capturing range of the tomographic image in the depth direction is adjusted to a constant range, based on the position of the predetermined reflector. In the process in S1, the control unit 30 may adjust the optical path length difference, for example, based on a signal output from the detector 19 which is a signal relating to the predetermined reflector whose distance from the deflector 71 is known. As a specific example, in a case where the light blocking member 61 is used as the reflector, the optical path length is adjusted so that an image of the light blocking member 61 is formed in the upper portion of the tomographic image as illustrated in FIG. 6. A target position of the image of the reflector in the tomographic image can be appropriately set in accordance with a distance (known value) between the deflector 71 and the reflector.

The process in S1 does not need to be performed every time the power of the apparatus is turned on, and may be performed every time the fiber 4 is exchanged. Alternatively, the process in S1 may be performed at any optional timing according to an instruction given from a worker or an assistant via the operation unit 42.

After completing the optical path length adjustment process (S1), the control unit 30 starts to perform the rotating operation of the fiber 4 and to switch on the measurement light source 11 and the aiming light source 12 (S2). In these operations, an operation already started in the optical path length adjustment process (S1) may be continued as it is. Alternatively, when the optical path length adjustment process (S1) is completed, the operation may be stopped once, and the process in S2 may be started again.

Thereafter, the processes in S3 to S10 (for the sake of convenience, S3 to S10 are collectively referred to as a "loop process") are repeatedly performed. The tomographic images are sequentially acquired at the same transverse position by performing the loop process. Based on the sequentially acquired tomographic images, a live image generated by the tomographic images is displayed on the display unit 41. Each frame of the live image according to the present embodiment is a synthetic image (also referred to as a synthesized tomographic image) obtained by synthesizing a plurality of sequentially acquired tomographic images. Hereinafter, in the present embodiment, a case will be described where an averaged image generated by the plurality of tomographic images is obtained as the synthetic image.

In an example in FIG. 6, the processes in S3 to S10 are performed all at once, thereby generating and displaying the live image for one frame by using the averaged image. Since the image of each frame is the averaged image, noise is restrained from affecting the live image. As a result, a worker can satisfactorily observe a structure of the subject on a real time basis.

In the loop process, first, a tomographic image acquisition process (S3) is performed by the control unit 30. In the tomographic image acquisition process (S3), based on a signal output from the detector 19, the control unit 30 newly generates at least one tomographic image, and causes a memory (for example, the RAM 32) to store the tomographic image. A series of these operations is referred to as "tomographic image acquisition". At least the process in S3 is performed once, thereby causing the memory (for example, the RAM 32) to accumulate a predetermined number of the tomographic images required for the averaged image. The memory may be a buffer memory for image (for example, a ring buffer). In the storage region of the memory, particularly a region which stores a plurality of the tomographic images processed for drawing the live image for one new frame is referred to as a "drawing region" for the sake of convenience. In the drawing region, a "latest image" and one of more "past images" are stored. The "latest image" described herein is one tomographic image acquired most recently. The "past image" is the tomographic image acquired in the past prior to the "latest image", and represents one or more tomographic images sequentially with the "latest image" in chronological order. In the following description, the drawing region has capacity enough to store the M-number of the tomographic images. The M-number can be appropriately set within a range equal to or greater than the number (N-number) required for generating the averaged image (however, M and N are both constants). In the following description, it is assumed that a relationship between M and N represents M>N. Every time a new tomographic image is acquired (in other words, whenever the "latest image" is updated), a pointer indicating a storing position of the latest image is moved. In accordance with the movement, an address of the drawing region is appropriately slid. For example, until the M-number of the tomographic images is stored in the drawing region, the tomographic images are repeatedly acquired. On the other hand, in a case where the M-number of the tomographic images is stored in the drawing region, the process in S4 is performed.

According to the present embodiment, the control unit 30 may perform a process (transforming process of image formats) for transforming the tomographic image from a RAW image format into a general purpose format such as bit map data. The control unit 30 may perform a contrast adjustment process for adjusting contrast of the tomographic image. In this case, the averaged image is generated from a plurality of the tomographic images in which each contrast is adjusted (details to be described later). Since the contrast is adjusted, it becomes easy to obtain a satisfactorily averaged image. In a flowchart in FIG. 6, each process such as the contrast adjustment may be performed as a part of the process in S3.

Next, the control unit 30 selects the tomographic image to be processed in order to draw the live image for one frame (S4). Here, the control unit 30 selects the M-number of the tomographic images stored in the drawing region.

Incidentally, the probe-type apparatus captures an image in a state where the probe 2 is gripped by a hand. Accordingly, it is conceivable that the camera is shaken by the hand when the image is captured (when the tomographic image is acquired). It is also conceivable that the subject side moves when the image is captured. For example, in a case where the inside of the eyeball is imaged, it is conceivable that the eyeball moves when the image is captured. Due to the influence of the relative movement between the probe 2 and the subject when the image is captured, there is a possibility that appearing positions of the image 110 of the subject may be different from each other, for example, between the plurality of tomographic images stored in the drawing region. There is a possibility that mutually different "shear strains" may occur between the plurality of tomographic images stored in the drawing region.

A case is also conceivable where scanning speed of the measurement light is uneven. In particular, the imaging apparatus 1 according to the present embodiment has a structure in which the measurement unit 10 (or an interference optical system) and the probe body 3 are connected by the fiber 4 so that the measurement light is used in scanning in response to the rotation of the fiber 4. According to this structure, resistance against the rotating movement of the fiber 4 varies depending on a bending state of the fiber 4. Consequently, the scanning speed of the measurement light is unlikely to be even (the scanning speed is likely to be uneven). Since the scanning speed of the measurement light is uneven when each tomographic image is acquired, there is a possibility that scaling in the scanning direction of the tomographic image may vary depending on each image.

Therefore, in a case where the averaged image is obtained by simply adding the plurality of tomographic images stored in the drawing region, an image like a ghost is drawn.

In contrast, according to the present embodiment, a correction process is performed in order to restrain the influence of the camera shake and the uneven scanning speed. The correction process is performed in order to correct at least any one of misalignment and distortion between the tomographic images. In a flowchart in FIG. 6, the correction process is illustrated as a position correction process (S5) and affine transformation (S6). However, as long as the correction process reduces the ghost in the averaged image, the correction process is not necessarily limited thereto.

In the position correction process (S5), mutual positions are corrected for the plurality (the M-number) of tomographic images selected in the process in S4. For example, the position correction process may be performed by performing pattern matching on the plurality of tomographic images. In this case, one sheet selected from the plurality of tomographic images is used as a template. The position correction process is performed by moving the respective tomographic images (including at least any one of parallel movement and rotating movement). In the following description, as a specific example, the latest image is used as the template. In other words, based on the latest image, each of the past images is moved, thereby correcting the position. Based on a matching result between the entire images (entire regions) in the respective tomographic images, the position may be corrected. Alternatively, based on a matching result between partial regions in the respective tomographic images, the position may be corrected. However, compared to a case where the position is corrected based on the matching result between the entire images, a processing time is shortened in a case where the position is corrected based on the matching result between the partial regions. Accordingly, the live image of each frame is likely to be smoothly drawn. As a result, it becomes easier to satisfactorily display the live image at a higher frame rate.

Here, referring to a flowchart in FIG. 7, a specific example of the position correction process (S5) will be described. In the specific example, first, a first position correction process is performed in which the positions of the plurality of tomographic images selected in the process in S4 are mutually corrected based on image information inside the light blocking portion area (S31).

More specifically, in the first position correction process (S31), the light blocking portion area in the respective tomographic images is specified by the control unit 30. The positions of the respective tomographic images are mutually corrected based on the image information inside the specified light blocking portion area (for example, the image information of the internally reflected image 101). That is, the first position correction process is performed by using only the information relating to a part of the tomographic image. Accordingly, although accuracy in correcting the position is relatively low, each image can be rapidly processed.

In particular, according to the present embodiment, as a result of the optical path length adjustment process (S1), the light blocking portion area is formed at a substantially constant position between the respective tomographic images. For example, as illustrated in FIG. 3, the light blocking portion area is formed at a predetermined position in the upper portion of the tomographic image. Therefore, it is easy to shorten a time required for acquiring the image information inside the light blocking portion area. As a result, the first position correction process (S31) is more rapidly performed.

Next, the respective tomographic images subjected to the first position correction process are transformed from the tomographic image expressed using the polar coordinate system into the tomographic image expressed using the Cartesian coordinate system (S32). According to this transformation process (S32), a shape of the image 110 of the subject is closer to an actual shape of an imaging target (here, the retina).

Next, a second position correction process (S33) is performed. The positions of the plurality of tomographic images whose positions are respectively corrected through the first position correction process (S31) are further specifically corrected through the second position correction process. In the second position correction process, based on the image information inside the opening portion area in the respective tomographic images, the positions of the respective tomographic images are mutually corrected.

More specifically, in the second position correction process (S33), the opening portion area in the respective tomographic images is specified by the control unit 30. The positions of the respective tomographic images are mutually corrected based on the image information inside the specified opening portion area (for example, the image information of the image 110 of the subject). In this manner, the image positions of the subject in the respective tomographic images very accurately match each other between the respective tomographic images.

In particular, here, the position correction using the image information inside the opening portion area is performed between the tomographic images expressed using the Cartesian coordinate system. In the tomographic image expressed using the Cartesian coordinate system, the shape of the image 110 of the subject is close to the actual shape. It is possible to very accurately perform the position correction by using the image 110 of the subject in this way.

Figure 7:
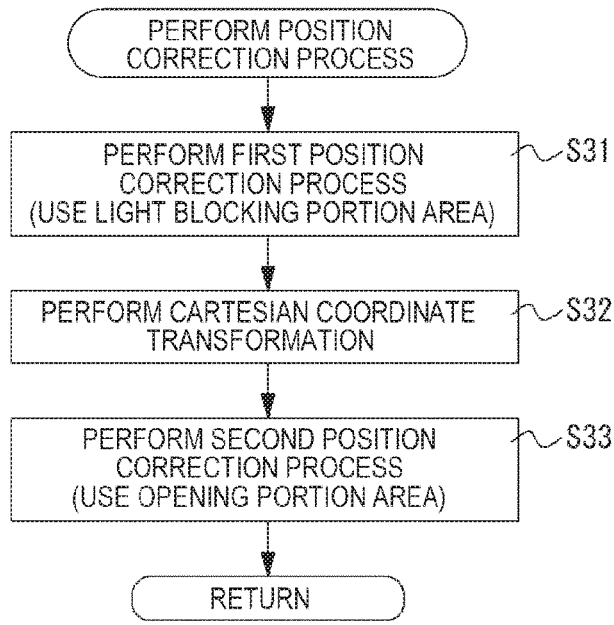
FIG. 7 is a flowchart illustrating a specific example of a correction process.

After the second position correction process (S33) is completed, the position correction process illustrated in FIG. 7 is completed. Then, the process returns to the flowchart in FIG. 6, and the process in S6 is subsequently performed.

In the process in S6, the affine transformation based on the template is performed on the plurality of tomographic images. In general, the affine transformation includes linear transformation (scaling, shear, and rotation) and parallel movement. In the process in S6, a deformation amount and a displacement amount may be calculated by setting the latest image as the template. Based on a calculated value, the linear transformation may be performed on each of the past images.

Here, the linear transformation may include at least any one of the scaling and the shear. In a case where the linear transformation using the shear is included in the process in S6, the "shear strain" of the tomographic images which is caused by the influence of the relative movement between the probe 2 and the subject during the image capturing is corrected. In a case where the linear transformation using the scaling is included in the process in S6, a scaling difference between the respective tomographic images which is caused by the uneven scanning speed is corrected. That is, in FIG. 6, the affine transformation (S6) is illustrated as an example of a process for correcting the scaling difference between the respective tomographic images in the scanning direction and a process for correcting the scaling difference between the respective tomographic images which is caused by the uneven scanning speed.

Next, a live image generation process (S7) is performed. In the live image generation process (S7), the averaged image displayed as the live image is generated based on the plurality (M-number) of tomographic images obtained after the position correction.

Figure 8:
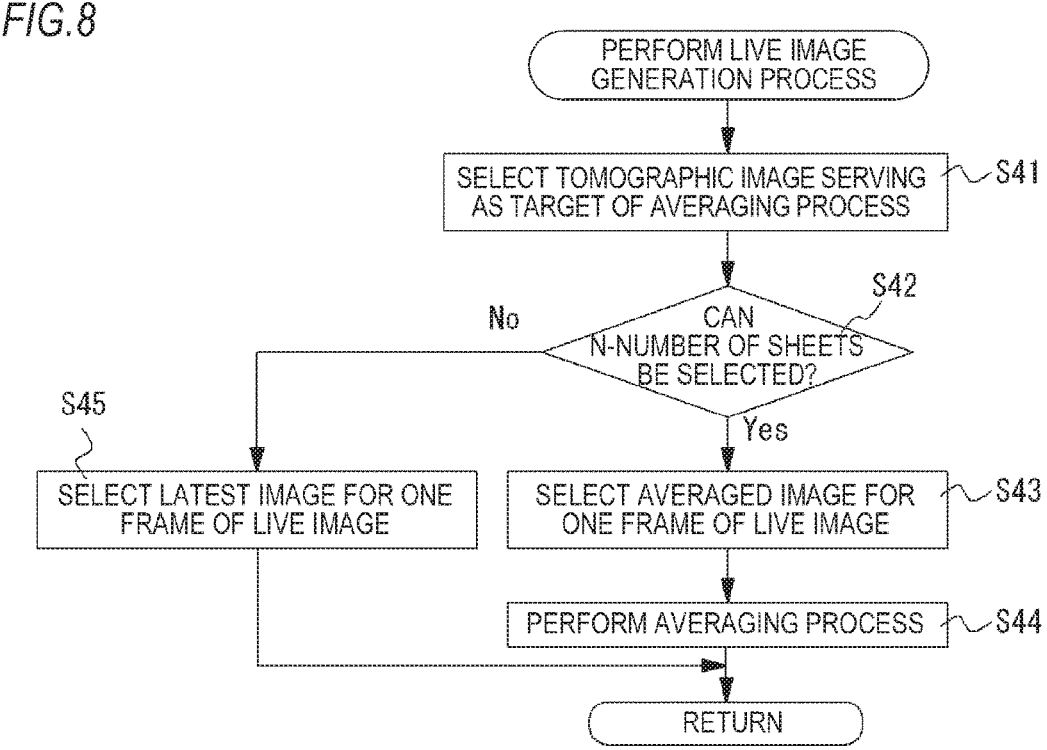
FIG. 8 is a flowchart illustrating a specific example of a live image generation process.

Here, FIG. 8 illustrates more detailed content of the live image generation process according to the present embodiment. In the live image generation process (S7), first, the N-number of sheets which are targets of the averaging process is selected from the plurality (M-number) of tomographic images whose positions are mutually corrected (S41). The N-number of selected sheets definitely includes the latest image. The remaining N−1 number of sheets is selected from the plurality of past images.

Figure 9:
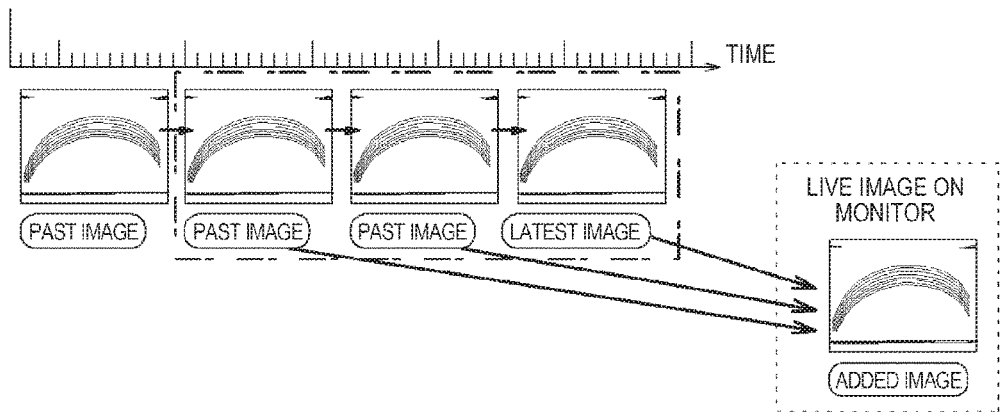
FIG. 9 is a schematic view illustrating an example of a selection method of a tomographic image displayed on a display unit.
Figure 9:
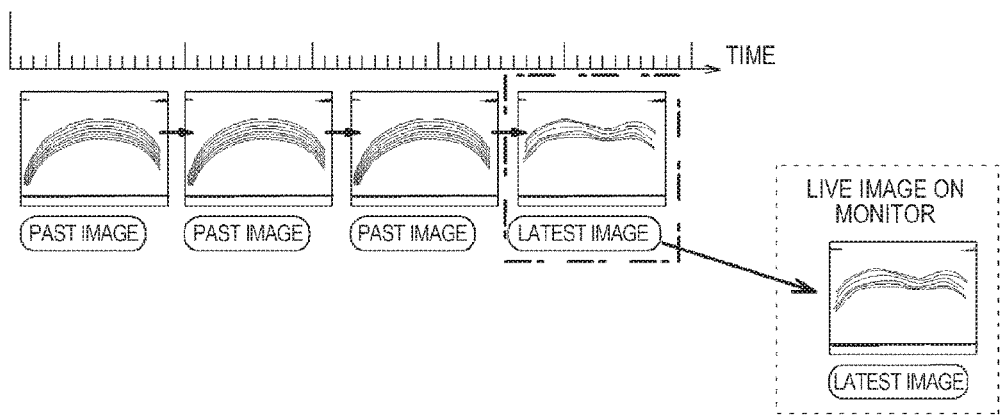
Figure 9:
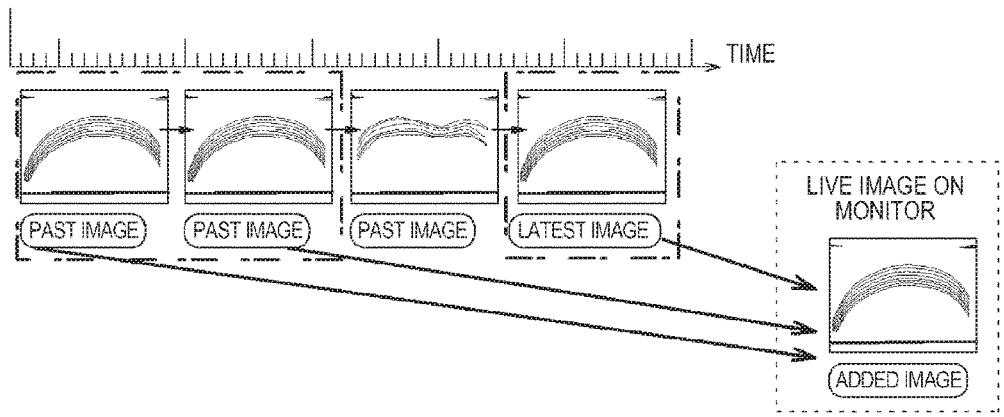

For example, FIG. 9 illustrates an outline of a selection method applicable to the process in S41. In an example in FIG. 9, the N−1 number of tomographic images is selected based on the following condition (1) and (2).

(1) The past image whose acquisition timing is closer to that of the latest image is preferentially selected.

(2) The past image is selected based on a pattern matching result between the respective past images and the latest image. For example, the pattern matching result may be obtained by performing a process for extracting a correlation coefficient (similarity degree) between two types of image. In this case, the past image in which the correlation coefficient does not satisfy a predetermined threshold is excluded from the target of the averaging process.

In a case where the N−1 number of past images is selected based on the conditions (1) and (2) (S42: Yes), the control unit 30 performs the averaging process on the selected past image and the latest image. The averaged image obtained as a result is obtained as the live image for one new frame (S43 and S44).

On the other hand, in a case where the N−1 number of past images cannot be selected since many images whose correlation coefficient (similarity degree) with the latest image does not satisfy the threshold are included in the plurality (M-number) of tomographic images obtained after the position correction (S42: No), the latest image is obtained as the live image for one new frame (S45).

A typical example of the case where many images whose correlation coefficient (similarity degree) with the latest image does not satisfy the threshold are included in the plurality (M-number) of tomographic images obtained after the position correction includes a case where the probe 2 and the subject are relatively moved. Therefore, in other words, in the live image generation process according to the present embodiment, (the presence or absence of) the relative movement between the subject and the probe 2 during video image capturing is detected by the control unit 30, based on the pattern matching result (or the correlation coefficient) between the plurality of tomographic images. Then, while the movement is detected, the latest image instead of the averaged image is displayed as the live image on the display unit. Therefore, it is conceivable that a worker is likely to quickly recognize a current position relationship between the probe 2 and the subject via the live images frequently displayed on the display unit. According to the present embodiment, in a case where the relative movement between the subject and the probe 2 is not detected, the video image to be displayed on the display unit is switched from the latest image to the averaged image by the control unit 30.

According to the present embodiment, the imaging apparatus 1 detects (the presence or absence of) the relative movement between the subject and the probe 2 during the video image capturing. However, a configuration is not necessarily limited thereto. For example, based on an image obtained by a device separate from the imaging apparatus 1 such as a surgical microscope, (the presence or absence of) the relative movement between the subject and the probe 2 may be detected. For example, in a case of the surgical microscope, the movement may be detected by using the aiming light. In a case where the movement is detected based on the image obtained by the device separate from the imaging apparatus 1, the movement detection process may be performed using a processing device (for example, a PC) separate from the imaging apparatus 1. In this case, a detection process result obtained by the processing device may be input to the control unit 30. In this manner, the control unit 30 may perform a process for selectively displaying the averaged image and the latest image as the live image. Detection means for detecting (the presence or absence of) the relative movement between the subject and the probe 2 is not necessarily limited to those which detect the movement based on the image. The movement may be detected based on a detection result obtained by using various sensors.

Referring back to FIG. 6, description will be continued. As a result of the live image generation process, the averaged image or the latest image obtained as the image for one frame in the live image is expressed using the Cartesian coordinate system through the coordinate transformation when the position is corrected. The live image may be expressed using the Cartesian coordinate system without any change. Alternatively, the coordinate transformation may be performed on the live image so as to be expressed using the polar coordinate system, and the live image obtained after the coordinate transformation may be displayed (S8 and S9). In this way, the live image for one frame is generated and displayed.

Next, the control unit 30 determines the presence or absence of an instruction to end the process (S10). If the instruction to end the process is not input, the process returns to the process in S3, and the live image is continuously generated and displayed. On the other hand, when the instruction to end the process is input, the process in the flowchart in FIG. 6 ends.

Hitherto, this disclosure has been described with reference to the embodiment. However, a technique included in this disclosure is not limited to the above-described embodiment, and can be varied in various ways.

For example, in the above-described embodiment, a case has been described as an example where the latest image and the past image which are formed from the tomographic images obtained at the same transverse position are synthesized through the averaging process so as to obtain one tomographic image as the synthetic image. However, a configuration is not necessarily limited thereto. Various synthetic processes in addition to the averaging process may be used. For example, the synthesis process may simply be an adding process. In the averaged image, luminance of a pixel after the pixel is synthesized has an average value of a pixel at a corresponding position before the pixel is synthesized. However, instead of the average value, the synthesis process may be performed using a value such as a mode value and a median value.

In the example in FIG. 6, whenever the power is turned on, the optical path length difference is always adjusted, but a configuration is not necessarily limited thereto. However, it is preferable to perform the process for adjusting the optical path length difference at least one or more times from when the fiber 4 (cable 4) until the tomographic image starts to be acquired (alternatively, until monitoring of a scanning failure starts).

In the above-described embodiment, a configuration has been described in which the deflector 71 of the probe 2 rotates together with the fiber 4, but a configuration is not necessarily limited thereto. For example, more specifically, as the deflector 71, a configuration may be used, such as a galvanometer mirror and an acousto optical modulator (AOM) which oscillate the laser light within a constant range.

The respective processes in the above-described embodiment (mainly, the processes illustrated in FIG. 6) may be partially applied to a stationary-type apparatus, for example, instead of the probe-type apparatus. The stationary-type apparatus described herein represents an apparatus an objective optical system for irradiating the subject (for example, the subject's eye) with the measurement light is fixedly disposed in a main body of the apparatus having the interference optical system disposed therein. Even if the above-described processes are applied to this apparatus, it is possible to enjoy the more excellent advantageous effect, compared to the related art.

What is claimed is:

1. An optical tomography apparatus comprising:
   a coupler configured to divide light output from a light source into measurement light and reference light;
   a detector configured to detect interference between the reference light and reflected light of the measurement light that is repeatedly scanned on a subject; and
   a processor configured to perform:
   an acquisition process of chronologically sequentially acquiring a plurality of tomographic images at the same transverse position in the subject are based on a signal output from the detector, and
   a video image generation process of generating a synthetic image on a real time basis by synthesizing a new tomographic image frequently obtained by the acquisition process and one or more past images which are the tomographic images acquired in the past prior to the new tomographic image and which are included in a range of a predetermined number of images whose acquisition timing is sequential to acquisition timing of the new tomographic image, and causing a monitor to display a real time video image formed from the synthetic image,
   wherein in the video image generation process, the processor performs a correction process of correcting at least any one of misalignment and distortion between the new tomographic image and the past image, and generates the synthetic image based on the respective tomographic images obtained after the correction process.

2. The optical tomography apparatus according to claim 1, wherein in the correction process, the processor corrects an entire image based on a matching result obtained in a partial region in the respective tomographic images.

3. The optical tomography apparatus according to claim 1, wherein
   the processor acquires the tomographic image expressed using a polar coordinate system in the acquisition process, and performs coordinate transformation on the new tomographic image and the past image so as to be transformed into the tomographic image expressed using a Cartesian coordinate in the video image generation process, and
   the correction process includes correction based on a matching result obtained by matching images of the subject after the coordinate transformation is performed on the new tomographic image and the past image.

4. The optical tomography apparatus according to claim 1, wherein the subject is radiated with the measurement light via a probe inserted into the subject.

5. The optical tomography apparatus according to claim 4, wherein
   in the video image generation process, the processor performs a correction process of correcting at least any one of misalignment and distortion between the new tomographic image and the past image, and generates the synthetic image based on the respective tomographic images obtained after the correction process, and
   the correction process includes first correction based on a matching result obtained in a first region which is a partial region of the respective tomographic images, which includes a reflected image relating to a structure of the probe, and which does not include the image of the subject, and second correction for further adjusting a position relationship of the respective tomographic images obtained after the first correction, and the second correction is performed based on a matching result obtained in a second region which is a partial region of the respective tomographic images, which includes the image of the subject, and which is located at a position different from that of the first region.

6. The optical tomography apparatus according to claim 4, wherein in the video image generation process, the processor performs a movement detection process for detecting a relative movement between the subject and the probe, and causes the monitor to display the new tomographic image instead of the synthetic image while the movement is detected.

7. The optical tomography apparatus according to claim 6, wherein in the video image generation process, in a case where the movement is detected and thereafter the movement is not detected, the processor switches the video image displayed on the monitor to the synthetic image.

8. An optical tomography apparatus comprising:
a coupler configured to divide light output from a light source into measurement light and reference light;
a detector configured to detect interference between the reference light and reflected light of the measurement light that is repeatedly scanned on a subject; and
a processor configured to perform:
an acquisition process of chronologically sequentially acquiring a plurality of tomographic images at the same transverse position in the subject are based on a signal output from the detector, and
a video image generation process of generating a synthetic image on a real time basis by synthesizing a new tomographic image frequently obtained by the acquisition process and one or more past images which are the tomographic images acquired in the past prior to the new tomographic image and which are included in a range of a predetermined number of images whose acquisition timing is sequential to acquisition timing of the new tomographic image, and causing a monitor to display a real time video image formed from the synthetic image,
wherein in the video image generation process, the processor selects one image from the new tomographic image and the past image, performs linear transformation including at least any one of shear and scaling on the remaining tomographic image, with reference to the selected tomographic image, and generates the synthetic image based on the selected tomographic image and the remaining tomographic image obtained after the linear transformation.

9. The optical tomography apparatus according to claim 8, wherein
the processor performs a selection process of selecting a target of a synthesis process using the new tomographic image in order to obtain the synthetic image, from the past images which are included in the range of the predetermined number of images whose acquisition timing is sequential to acquisition timing of the new tomographic image, and
in the selection process, the processor determines whether or not each of the past images is the target of the synthesis process, based on a pattern matching result between each of the past images and the new tomographic image, and selects the target based on the determination result.

10. The optical tomography apparatus according to claim 9, wherein in the selection process, in a case where the number of past images determined as the target of the synthesis process is equal to or greater than a predetermined number of synthetic images, the processor preferentially selects the tomographic image whose acquisition timing is close to the acquisition timing of the new tomographic image, as the target of the synthesis process.

11. The optical tomography apparatus according to claim 9, wherein in a case where the number of past images determined as the target of the synthesis process by performing the selection process does not satisfy a predetermined number of synthetic images, in the video image generation process, the processor causes the monitor to display the new tomographic image instead of the synthetic image.

12. An optical tomography apparatus comprising:
a coupler configured to divide light output from a light source into measurement light and reference light;
a detector configured to detect interference between the reference light and reflected light of the measurement light that is repeatedly scanned on a subject; and
a processor configured to perform:
an acquisition process of chronologically sequentially acquiring a plurality of tomographic images at the same transverse position in the subject are based on a signal output from the detector, and
a video image generation process of generating a synthetic image on a real time basis by synthesizing a new tomographic image frequently obtained by the acquisition process and one or more past images which are the tomographic images acquired in the past prior to the new tomographic image and which are included in a range of a predetermined number of images whose acquisition timing is sequential to acquisition timing of the new tomographic image, and causing a monitor to display a real time video image formed from the synthetic image, wherein
the processor performs a selection process of selecting a target of a synthesis process using the new tomographic image in order to obtain the synthetic image, from the past images which are included in the range of the predetermined number of images whose acquisition timing is sequential to acquisition timing of the new tomographic image, and
in the selection process, the processor determines whether or not each of the past images is the target of the synthesis process, based on a pattern matching result between each of the past images and the new tomographic image, and selects the target based on the determination result.

13. The optical tomography apparatus according to claim 12, wherein in the selection process, in a case where the number of past images determined as the target of the synthesis process is equal to or greater than a predetermined number of synthetic images, the processor preferentially selects the tomographic image whose acquisition timing is close to the acquisition timing of the new tomographic image, as the target of the synthesis process.

14. The optical tomography apparatus according to claim 12, wherein in a case where the number of past images determined as the target of the synthesis process by performing the selection process does not satisfy a predetermined number of synthetic images, in the video image generation process, the processor causes the monitor to display the new tomographic image instead of the synthetic image.

* * * * *